(12) United States Patent
Connolly

(10) Patent No.: US 10,716,490 B2
(45) Date of Patent: Jul. 21, 2020

(54) WOUND DRESSING WITH IMPEDANCE SENSOR

(75) Inventor: Patricia Connolly, Glasgow (GB)

(73) Assignee: University of Strathclyde, Glasgow (GB)

(*) Notice: Subject to any disclaimer, the term of this patent is extended or adjusted under 35 U.S.C. 154(b) by 0 days.

(21) Appl. No.: 13/379,309

(22) PCT Filed: Jul. 9, 2010

(86) PCT No.: PCT/GB2010/001320
§ 371 (c)(1),
(2), (4) Date: Mar. 27, 2012

(87) PCT Pub. No.: WO2011/004165
PCT Pub. Date: Jan. 13, 2011

(65) Prior Publication Data
US 2012/0190956 A1    Jul. 26, 2012

(30) Foreign Application Priority Data
Jul. 10, 2009   (GB) .................................... 0912009.8

(51) Int. Cl.
*A61B 5/04*    (2006.01)
*A61B 8/00*    (2006.01)
(Continued)

(52) U.S. Cl.
CPC ............ *A61B 5/0537* (2013.01); *A61B 5/445* (2013.01); *A61B 5/4869* (2013.01); *A61B 5/685* (2013.01); *A61F 13/025* (2013.01); *A61F 13/0233* (2013.01); *A61F 13/0253* (2013.01); *A61F 13/0276* (2013.01); *A61B 2562/0215* (2017.08); *A61B 2562/12* (2013.01); *A61F 2013/00204* (2013.01); *A61F 2013/00442* (2013.01); *A61F 2013/00944* (2013.01); *A61F 2013/00961* (2013.01); *Y10T 29/49002* (2015.01); *Y10T 156/10* (2015.01)

(58) Field of Classification Search
CPC .. A61N 1/0456; A61N 1/0468; A61N 1/0492; A61B 5/445; A61B 5/0531
USPC ................ 600/372, 382, 384, 386, 391–393, 600/395–396
See application file for complete search history.

(56) References Cited

U.S. PATENT DOCUMENTS 4,370,984 A * 2/1983 Cartmell ............ A61B 5/04026
600/385
4,573,480 A   3/1986 Hirschberg
(Continued)

FOREIGN PATENT DOCUMENTS

CN    1865341 A    11/2006
CN    101049261 A  10/2007
(Continued)

OTHER PUBLICATIONS

International Search Report dated Sep. 22, 2010 for Application No. PCT/GB2010/001320.
(Continued)

*Primary Examiner* — Eun Hwa Kim
*Assistant Examiner* — Brian M Antiskay
(74) *Attorney, Agent, or Firm* — Alston & Bird LLP

(57) ABSTRACT

A wound sensor comprising at least one electrode (10a, 10b) and a non-adherent porous layer (25) proximate at least part of the electrode.

59 Claims, 5 Drawing Sheets

(51) Int. Cl.
*A61B 5/053* (2006.01)
*A61B 5/00* (2006.01)
*A61F 13/02* (2006.01)
*A61F 13/00* (2006.01)

(56) References Cited

U.S. PATENT DOCUMENTS

| | | | |
|---|---|---|---|
| 4,580,233 A | | 4/1986 | Parker et al. |
| 4,603,704 A | | 8/1986 | Mund et al. |
| 4,611,604 A | | 9/1986 | Botvidsson et al. |
| 5,218,973 A | | 6/1993 | Weaver et al. |
| 5,276,079 A | * | 1/1994 | Duan et al. ............ 524/386 |
| 5,466,252 A | | 11/1995 | Soukup et al. |
| 5,622,168 A | * | 4/1997 | Keusch et al. ............ 600/391 |
| 6,200,250 B1 | | 3/2001 | Janszen |
| 6,301,500 B1 | * | 10/2001 | Van Herk ............ A61B 5/0531 600/393 |
| 7,945,302 B2 | | 5/2011 | McAdams |
| 9,526,439 B2 | | 12/2016 | Connelly et al. |
| 2002/0034492 A1 | | 3/2002 | Munro et al. |
| 2002/0198483 A1 | | 12/2002 | Wariar et al. |
| 2003/0216663 A1 | | 11/2003 | Jersey Willuhn et al. |
| 2003/0216783 A1 | | 11/2003 | Lehtoluoto |
| 2004/0036484 A1 | | 2/2004 | Tamai |
| 2006/0047218 A1 | | 3/2006 | Bloom et al. |
| 2006/0052678 A1 | | 3/2006 | Drinan et al. |
| 2006/0258788 A1 | | 11/2006 | Coggins et al. |
| 2006/0270942 A1 | * | 11/2006 | McAdams ............ 600/547 |
| 2008/0063695 A1 | | 3/2008 | Vitaris |
| 2008/0171957 A1 | | 7/2008 | Connelly et al. |
| 2008/0319292 A1 | * | 12/2008 | Say et al. ............ 600/347 |
| 2013/0116635 A1 | | 5/2013 | Fleischmann |

FOREIGN PATENT DOCUMENTS

| | | |
|---|---|---|
| CN | 101123930 A | 2/2008 |
| CN | 101279102 A | 10/2008 |
| DE | 3223036 | 12/1983 |
| DE | 4014572 | 11/1991 |
| EP | 0403608 | 12/1990 |
| FR | 2682487 | 4/1993 |
| FR | 2692487 A1 | 12/1993 |
| GB | 2362466 | 11/2001 |
| JP | 05-261145 A | 10/1993 |
| JP | 06-205825 A | 7/1994 |
| JP | 09-038214 A | 2/1997 |
| JP | 9-33468 | 7/1997 |
| JP | 10-295726 | 11/1998 |
| JP | 2002-224093 | 8/2002 |
| JP | 2002-325740 A | 11/2002 |
| JP | 2004-85277 | 3/2004 |
| JP | 2005-532841 A | 11/2005 |
| JP | 2006-508732 A | 3/2006 |
| JP | 2007-532220 A | 11/2007 |
| WO | WO 90/05026 | 5/1990 |
| WO | WO 03/063680 A2 | 8/2003 |
| WO | WO 2004/049937 | 6/2004 |
| WO | WO 2005/099644 | 10/2005 |
| WO | WO 2009/092616 | 7/2009 |
| WO | WO-2011/004165 A1 | 1/2011 |

OTHER PUBLICATIONS

Office Action dated Jun. 2, 2010 for European Application No. 05 738 126.1.
International Search Report dated Oct. 10, 2005 for Application No. PCT/GB2005/001483.
International Preliminary Report on Patentability dated Jul. 17, 2006, for Application No. PCT/GB2005/001483.
Office Action dated May 18, 2010, for U.S. Appl. No. 11/578,526.
Office Action dated Nov. 9, 2010 for U.S. Appl. No. 11/578,526.
Intellectual Property Office, Search Report for Application No. GB0912009.8, dated Sep. 15, 2009, 1 page, United Kingdom.
Japan Patent Office, First Office Action for Application No. 2012-519056, dated Apr. 1, 2014, 11 pages, Japan.
Sood, A., et al., "Wound Dressing and Comparative Effectiveness Data", *Advances in Wound Care*, submitted for publication Dec. 23, 2012, pp. 511-529, vol. 3, No. 8, Mary Ann Liebert, Inc., U.S.A.
McColl, David, et al., "Monitoring moisture without disturbing the wound dressing", Wounds UK, 2009, pp. 94-99, vol. 5, No. 3, UK.
The State Intellectual Property Office of the P.R.C., First Office Action, including Search Report, for Application No. 20108003098. X, dated Dec. 26, 2013, 30 pages, China.

* cited by examiner

WOUND DRESSING WITH IMPEDANCE SENSOR

CROSS REFERENCE TO RELATED APPLICATIONS

This application is a national stage application, filed under 35 U.S.C. § 371, of International Application No. PCT/GB2010/001320, filed Jul. 9, 2010, which claims priority to Great Britain Application No. 0912009.8, filed Jul. 10, 2009, both of which are hereby incorporated by reference in their entirety.

BACKGROUND

Related Field

The present invention relates to a sensor. In particular, the present invention relates to a sensor for determining the status of a wound.

Description of Related Art

It is useful to be able to monitor the status of a wound, for example, to check on the rate of healing of the wound and/or to determine if the wound dressing or treatment is optimally arranged. Sensors for monitoring wounds have been suggested to monitor a variety of parameters including pH, temperature, tissue closure, infection, biomarkers of healing, enzymes and moisture. In practice almost nothing has been demonstrated on live patients in the clinic due to the difficulty of creating an economical sensor made of non-toxic, sterilisable materials that may stay on a wound or in a wound dressing without causing interference to the healing process.

Moisture at the wound to dressing interface or in the wound dressing is important to measure. This is because maintaining a correct level of moisture in the wound can be important to prevent the wound getting too wet or too dry. Optimal healing in most wounds occurs only in moist conditions. Wet wounds macerate and tissue breaks down further. Dry wounds do not heal well if they are large area or they heal but often with adherence to the wound dressing causing pain and damage on dressing removal.

Wound monitoring is often difficult, as it may require removal of a wound dressing, which can affect healing. Wound monitoring sensors are available, but these can be problematic, as such sensors may use materials that interfere with or irritate the wound. Array sensors taking the form of patterns on insulating material have been suggested. However, in practice, these occlude the wound and can cause skin maceration. Also, some types of sensors adhere to the wound, which can result in wound damage when they are removed. Some sensors also interfere with the healing of the wound by interfering with moisture control, whilst some only have a limited lifetime in a wound environment and are affected by exudates, blood or other wound materials. Also, it has proved difficult to date to provide a moisture sensor for the clinical field that can quantify the moisture present in a wound dressing into moisture scales such as dry-moist—wet, allowing a clinician to make a decision on dressing change without removing the dressing.

EP 0,403, 608 A describes a sensor for wound dressings that includes a temperature sensitive colour change materials. Since change of blood flow and infection in a wound can change temperature this could have some usefulness if a stable and non-toxic material could be found and formed so as to stay in contact with skin.

DE 4014572 A1 describes a moisture system for sensing blood in bandages. This combines a dc resistance measurement for detecting wetness and an optical sensor for detecting characteristic colours of blood. The dc measurement can, however, cause electrochemistry and dissolution of the electrode causing the formation of new chemicals in the vicinity of the wound, or releasing components of the electrode, introducing possible toxic effects and changing the wound healing environment from its natural condition. Also, the variation in ionic content and ionic mobility of wound exudate makes the dc resistance very variable. For example in thick exudate that is still moist a very high dc resistance may be presented that will not trigger threshold wetness.

JP 2002-224093 describes a printed sensor for moisture detection in a diaper. The sensor described detects wetness through a change in the inherent capacitance of the sensor itself. It is constructed so that the electrostatic field of the sensor electrodes is altered in the presence of moisture introducing localised changes in impedance which are essentially changes to the capacitance of the sensor. Between the sensing electrodes there is always a completely insulating layer to provide a fixed dry capacitance and known electrostatic field. The impedance changes introduced are relatively small and not quantitative but setting a threshold at each sensor in the array allows the spread of unquantified levels of wetness to be detected. This device detects a pattern of 'wet' or 'non-wet' across the sensor array.

JP 295726 describes a moisture sensor that traps urine in a fixed layer and indicates that moisture is present. It is unsuitable for wound contact because it is designed to trap liquid between electrodes in a water absorbing layer protected by a water impermeable outer barrier. This is said to work for diapers because it will always trap liquid and therefore the device will always show when urination has occurred even if it was some time prior to the device being read. No quantification of the moisture in the diaper or monitoring with time can occur.

JP 2004 85277A describes a moisture sensor that is only suitable for use in an outside layer of a dressing or bandage and needs to be covered by a moisture impermeable material with a hole in it. The moisture impermeable material is designed to protect the effective capacitor between the sensor electrodes that will change capacitance when moisture enters the hole or water permeable layer in the device. The device will fail in use in wound dressings because the moisture impermeable barrier that protects the sensor will trap wound exudate and cause maceration of the skin. Also this device detects wet or dry, but has no capacity for detection of different quantities of moisture.

WO2004/049937 and WO29092616A describe an array of rectangular electrodes that may be used to stimulate wound tissue electrically or measure impedance of wound tissue. The measurement electrodes are isolated from each other by a blocking layer, such as a dried out non-conducting hydrogel. In use, the conducting parts of the stimulating electrodes in direct contact with wound tissue via a hydrogel patch on the exposed conducting electrode. Thus, they are designed to be electrically connected to the tissue but not to measure moisture above the wound or at a localised site between the electrodes. In practice, allowing the electrodes to dry into healing tissue and stick to the healed cell layer. Removal of the device with the wound dressing would remove the healed skin. Application of a hydrogel to the electrodes does little to alleviate the problem as this too will dry out during the healing process.

FR 2682487 describes a single patch electrode that is in effect a conducting mesh that can be applied to live tissue for delivery of voltage or current to stimulate that tissue. It is designed specifically for the relatively high voltages and current used to defibrillate the heart and is intended for placement directly on to cardiac tissue. Such a conducting mesh will make random contact with both tissue, blood and moisture and, in contact with living tissue, will have a random self-impedance that changes according to the proteins and cells that move around or on the tissue. Thus it is not suitable for the monitoring of moisture only in a wound dressing and unlikely to be very suitable for the delivery of electrical therapy to a healing wound. The construction of the sensor makes it unsuitable for use as a 'paired electrode' if local impedance measurements were required over a localised area.

U.S. Pat. No. 4,611,604 describes an electrode to be used as a return or passive electrode in a heart pacemaker. The electrode is a metal coated with a porous material and has a high double layer capacitance. The porous layer coating of the electrode is conducting and is a nitride, carbide or some such equivalent. Thus, the porous layer is part of the electrode and is electrically connected to it. U.S. Pat. No. 4,603,704 describes a further development of such a high double layer capacitance system in an individual electrode for voltage stimulation.

U.S. Pat. No. 4,573,480 describes another electrode arrangement for use in a cardiac pacemaker. This has porosity to give it flexibility but cannot be entered by body fluids. This is useful in an insulating environment but not suitable as a coating for a moisture sensor. Others have combined electrode shapes and insulating coatings, including flexible outer layers such as in U.S. Pat. No. 5,466,252. Again this type of device is useful for implantable, insulated electrodes for heart stimulating, but not for localised moisture monitoring in wound dressings.

WO099644A2 describes the use of ac impedance and frequency selection to quantify moisture levels within a wound dressing or at a wound interface. Moisture levels can be monitored quantitatively with time. This allows exudate flow to be monitored with time and dressing performance and hydration in various locations to be monitored.

Although a variety of tissue sensors and electrodes are known, care must be exerted in monitoring devices that may be in contact with skin, whether health, damaged or diseased, so that (a) the device does not cause more local tissue damage and (b) the device correctly monitors the parameter of medical or care interest.

BRIEF SUMMARY

According to a first aspect of the present invention, there is provided a wound sensor comprising at least one electrode and a non-adherent porous layer proximate at least part of the electrode.

The invention provides a moisture sensor capable of grading levels of moisture in a wound dressing at the wound surface or within the wound dressing without interfering with the healing process. The sensor is capable of being left in place in the dressing for long periods of time during the healing period.

Non-adherent as used herein is defined as being adapted to resist adherence to a wound or healing tissue.

The porous layer may be a medically acceptable surface, material or coating, such as a biocompatible and/or non-irritant surface, material or coating.

The sensor may contain two or more electrodes. The at least one electrode may be disposed on a substrate. The substrate may be a non-adherent substrate. The substrate may be an electrically insulating substrate. The substrate may be adapted to ensure minimal occlusion of the healing wound, allowing moisture transfer from the wound to its surroundings.

The non-adherent porous layer may be adjacent to at least part of the electrode. The sensor may be arranged such that, in use, the non-adherent porous layer is provided on an opposite side of the electrodes to the substrate.

The non-adherent porous layer may comprise silicone, for example a non-adherent porous silicone coating. The silicone coating may advantageously resist wound adhesion.

The non-adherent porous layer may comprise a cellulosic material, such as a knitted viscose or acetate non-adherent wound contact material.

The non-adherent porous layer may range in thickness from μm to millimetres and preferably in the range of 50-500 μm.

The non-adherent porous layer may have pore sizes in the range of μm to mm, and advantageously from 20-500 μm.

The non-adherent porous layer may introduce what can be considered a small volume electrochemical cell into which flows the wound exudate, separating it from the wound surface for accurate measurement of its electrical properties.

Importantly a sterile sensor with the non-adherent porous layer may be left in place during the lifetime of a wound dressing whilst minimising any detrimental affects on wound healing.

The non-adherent porous layer may comprise a single layer. The single layer may overlie the electrodes. The single layer may overlie the electrodes, without being directly physically connected to the electrodes. The single layer may be a single layer of fabric. The single layer may be made of one or more materials.

The sensor may be arranged such that, in use, the non-adherent porous layer is located towards a wound and/or the substrate located away from the wound.

The electrode may comprise a sensing surface for taking electrical measurements. The sensing surface may be adjacent the non-adherent porous layer. The at least one electrode may comprise a signal carrying portion for carrying an electrical signal to and/or from a controller. The sensor may comprise at least one contact pad for connecting to the controller.

The electrode may comprise a biocompatible material. The electrode may comprise silver and/or a silver containing compound, such as silver chloride. The electrode may be a silver/silver chloride electrode. The electrode may comprise a metal and/or a metal containing compound such as gold, platinum and/or a compound thereof and/or a carbonaceous material, such as graphite.

The electrodes may be at least partially formed from conductive ink. The electrodes may comprise wires.

The electrodes may be elongated. By having thin, elongated electrodes, the surface area covered by the electrode may be minimised, reducing interference with the normal function of the wound dressing and/or healing of the wound.

The electrodes may be bonded to wires. The bond may comprise a conductive epoxy and/or solder, which may be arranged to not contact the wound in use.

The sensor may further comprise an electrically insulating layer. At least part of the electrode may be provided between the substrate and the insulating layer. At least part of the signal carrying portion of the electrode may be provided between the substrate and the insulating layer. The insulating layer may be adhered to and/or pressed together with and/or integral with the substrate around the signal carrying part of the electrode. The insulating layer may be arranged such that the sensing surface is not covered by the insulating layer.

The substrate and/or insulating layer may comprise a biocompatible, flexible polymer films approved for wound contact. The substrate and/or insulating layer may comprise a polyolefin film, such as a polyethylene film. The polyethylene film may be a low density polyethylene film. The substrate and/or insulating layer may be at least partially coated with an adhesive, which may be an acrylic adhesive. An example of a suitable substrate and/or insulating layer material is Scapa (RTM) Bioflex (RTM) RX607P. The substrate may comprise two layers of polyolefin film adhered together. The substrate may be between 0.075 mm and 1 mm thick.

The sensor may be arranged to be used with, and/or be part of, a wound dressing. The sensor may be arranged such that, in use, the substrate faces the wound dressing, whilst the non-adherent porous layer and the exposed sensing surfaces of the electrodes face the wound.

The sensing surfaces may be arranged to perform electrical stimulation of the wound.

According to a second aspect of the invention, there is provided a wound dressing comprising a sensor of the first aspect.

The sensor may be arranged such that the substrate is located towards the wound dressing and the non-adherent porous layer is located away from the wound dressing. The wound dressing may be arranged such that, in use, the non-adherent porous layer and the exposed sensing surfaces of the electrodes face the wound.

According to a third aspect of the present invention, there is provided a system comprising a sensor of the first aspect and a controller.

The controller may be arranged to determine impedance and preferably, arranged to perform AC impedance spectroscopy, using the sensor. The controller may comprise a processor and/or memory. The controller may be adapted to store a look-up table, for determining a status of a wound based on the determination of impedance. The controller may be arranged to display a status of the wound dressing.

The controller may be arranged to determine a status of the wound using the real and/or imaginary components of one or more AC impedance measurements.

The controller may be arranged to determine viscosity of wound exudates and/or determine if a wound is becoming infected based on AC impedance measurements. For example, in drying wounds some aspects of the reactive component of impedance may change with viscous exudates.

The controller may be arranged to apply an electrical signal to the electrodes in order to perform electrical stimulation of the wound. The controller may be arranged to apply a current in the order of μA to mA.

The controller may be arranged to apply a voltage in the range 5 to 200 mV.

The controller may be arranged to apply a frequency in the range 0.1-100 kHz.

Typically the wound sensor/dressing remains in place for one to seven days. Measurements may be taken daily, every two hours or continuously depending on the information needed.

According to a fourth aspect of the present invention, there is provided a method of determining a status of a wound comprising providing a sensor of the first aspect and determining impedance using the sensor.

The method may comprise determining impedance using AC impedance spectroscopy. The method may comprise determining real and/or imaginary impedance components using the sensor. The method may comprise using the determined impedance, and preferably using the determined real and/or imaginary components of at least one AC impedance measurement, in order to determine a wound status such as the level of moisture present and/or viscosity of exudate from a wound and/or whether a wound is becoming infected.

The invention is such that the sensor may remain in place during healing. The time duration or time-related healing of the wound may be followed. For example, as moisture at the wound interface is important, the sensor and impedance method can be used as a one off measurement to check moisture status (or need to change dressing) or the system can be deployed to track, intermittently or continuously, the moisture course of the wound as it heals. Thus specific interventions may be made related to rate of moisture change, such as moisture change per day, which are only possible through sensors that can remain in the healing area for long periods of time without disturbing the healing process. Such interventions may be made specific to best practice dependent on wound type, i.e. an ideal moisture/healing profile may be different for a venous leg ulcer as compared to a pressure sore.

The method may comprise placing the sensor on a wound such that the non-adherent porous layer faces the wound, such that the non-adherent porous layer is located between the electrodes and the wound.

The controller may be arranged to measure ac impedance at selected frequencies or in a frequency range.

The controller may be arranged to measure electrical properties such as ac impedance or apply electrical stimulation of the wound.

According to a fifth aspect, there is provided a method of fabrication a sensor comprising providing at least one electrode and a non-adherent porous layer adjacent at least part of the electrode. The method may comprise providing a non-adherent porous layer adjacent at least a sensing surface of the electrode. The electrode may be an electrode of the first aspect.

The electrode may be provided on a substrate. At least part of the electrode may be located between the substrate and an insulating layer.

The method may comprise attaching the insulating layer and/or at least part of the electrodes and/or the substrate to the non-adherent porous layer. The non-adherent porous layer may be adhesively attached. The non-adherent porous layer may be adhesively attached using a medical device adhesive, which may comprise an acrylate adhesive such as a cynoacrylate adhesive, for example, an adhesive comprising ethyl cyanoacrylate. The adhesion of the porous layer may be provided by a non-continuous layer of adhesive, preferably by spots of adhesive.

The method may comprise providing a patterned ink layer on at least part of the substrate; and processing the patterned ink to form at least one electrode.

The ink may comprise at least one metallic substance and or a metal salt. The ink may comprise silver, gold, platinum and/or carbon, such as graphite, and/or a compound thereof. The ink may be a silver/silver chloride ink.

The processing may comprise curing the ink. The processing may comprise heating the ink above a threshold temperature for a threshold time in order to form at least one electrode. Other methods of curing may be appropriate for other inks and polymers such as UV curing.

The ink pattern may be applied by screen printing. The ink pattern may be applied by gravure printing, reverse gravure printing, doctor blade, ink-jet printing, and/or flexographic printing.

The method may comprise applying the insulating layer to at least part of the electrodes and/or substrate. The method may comprise leaving a portion of the electrodes uncovered by the insulating layer. The uncovered portion of the electrodes may comprise the sensing surface. The insulating layer may be applied by adhesive bonding. The insulating layer may be applied using an acrylic adhesive.

The method may comprise removing an excess of substrate and/or insulating layer. In this way, the sensor may provide a minimal surface area so as to minimise interference of the wound healing process and minimise the barrier to wound fluids such as exudates and/or blood from passing from the wound to a wound dressing or an outer surface.

BRIEF DESCRIPTION OF THE FIGURES

Various aspects of the invention will now be described by way of example only with reference to the accompanying drawings, of which.

DETAILED DESCRIPTION OF VARIOUS EMBODIMENTS

Figure 1:
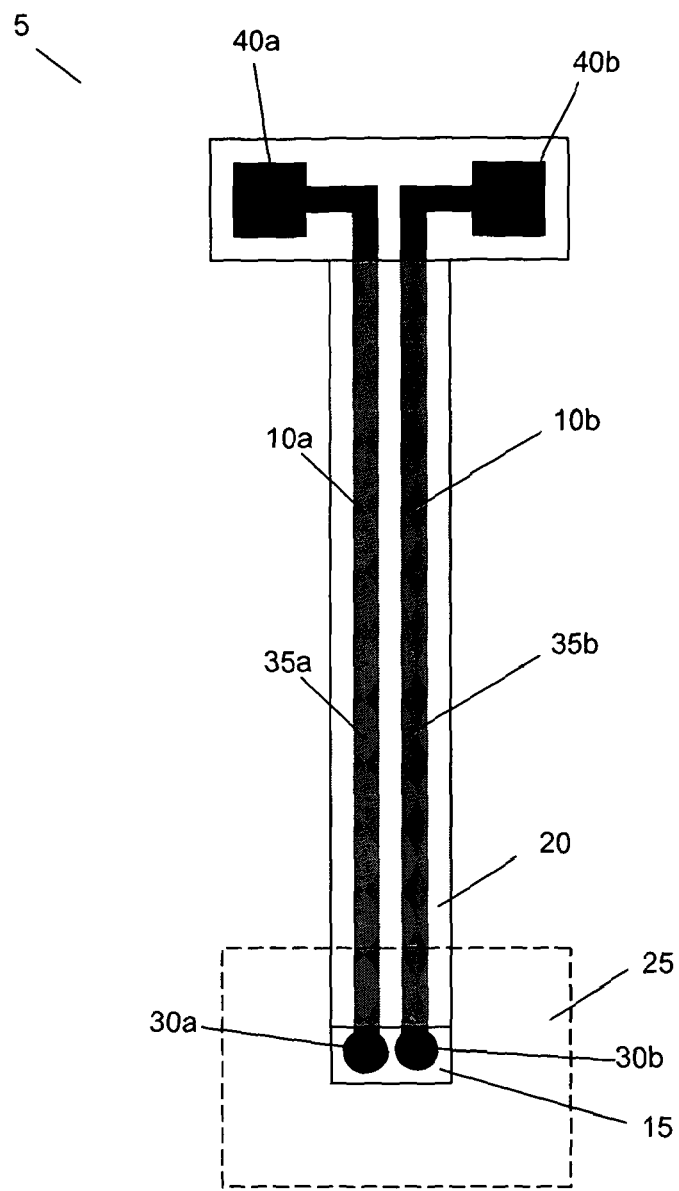
FIG. 1 is a schematic of a wound sensor.
Figure 2:
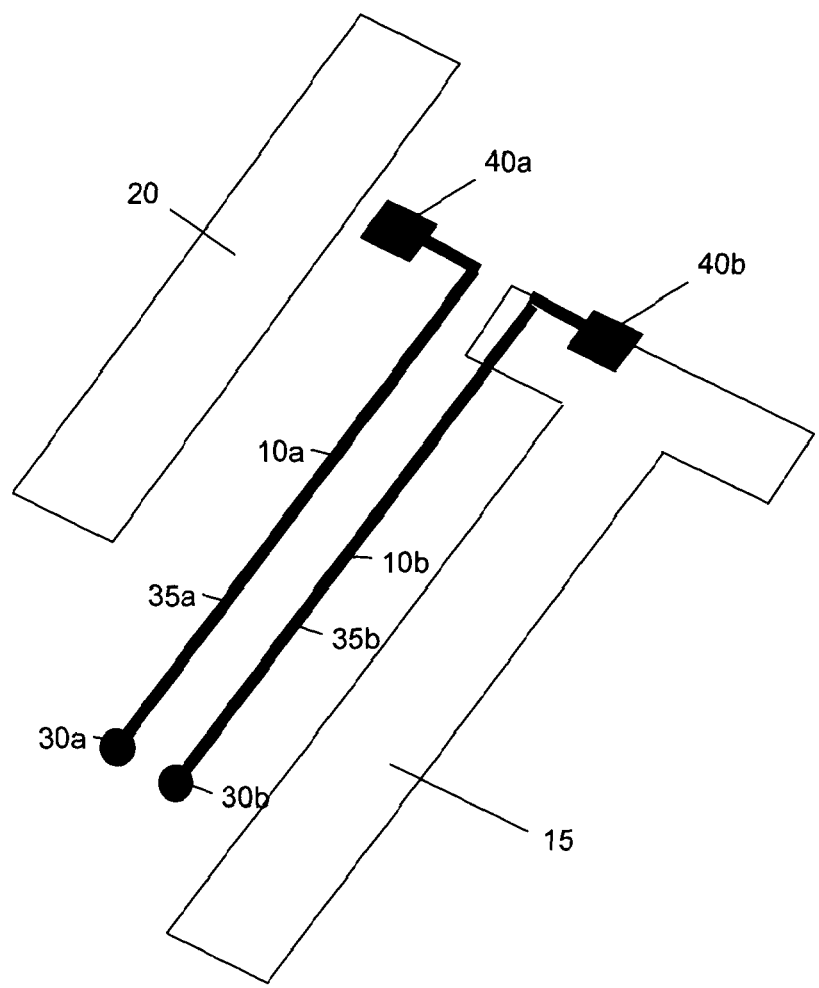
FIG. 2 is an exploded view of the sensor of FIG. 1.

FIG. 1 shows a sensor 15 comprising two electrodes 10a, 10b on a substrate 15 that is made of an electrically insulating material, the electrodes 10a, 10b being covered by a single layer of non-adherent porous material 25. The electrodes 10a, 10b are screen-printed silver/silver chloride electrodes that have a natural antimicrobial function and can discourage protein adhesion and microbial growth.

FIGS. 2 to 5 show the electrodes 10a, 10b in more detail. Each has a sensing surface 30a, 30b, a signal carrying portion 35a, 35b and a contact pad 40a, 40b arranged for connection to a controller. The sensing surface 30a, 30b is arranged for obtaining electrical measurements, whilst the signal carrying portion 35a, 35b is arranged to carry signals between the sensing surface 30a, 30b and the contact pad 40a, 40b.

Adhered to the substrate 15 using a medical grade adhesive is an insulating layer 20. The signal carrying portions 35a, 35b of the electrodes 10a, 10b are sandwiched between the insulating layer 20 and the substrate 15. The insulating layer 20 is bonded to the substrate 15 around the signal carrying portions 35a, 35b of the electrodes 10a, 10b. The insulating layer 20 is sized so that it substantially covers signal carrying portions 35a, 35b, but leaves exposed the sensing surfaces 30a, 30b and the contact pads 40a, 40b. In this way, only a paired, localised sensing surface area 30a, 30b of the electrodes is exposed to the wound. This allows localised, controlled and reproducible measurements to be made.

Figure 5:
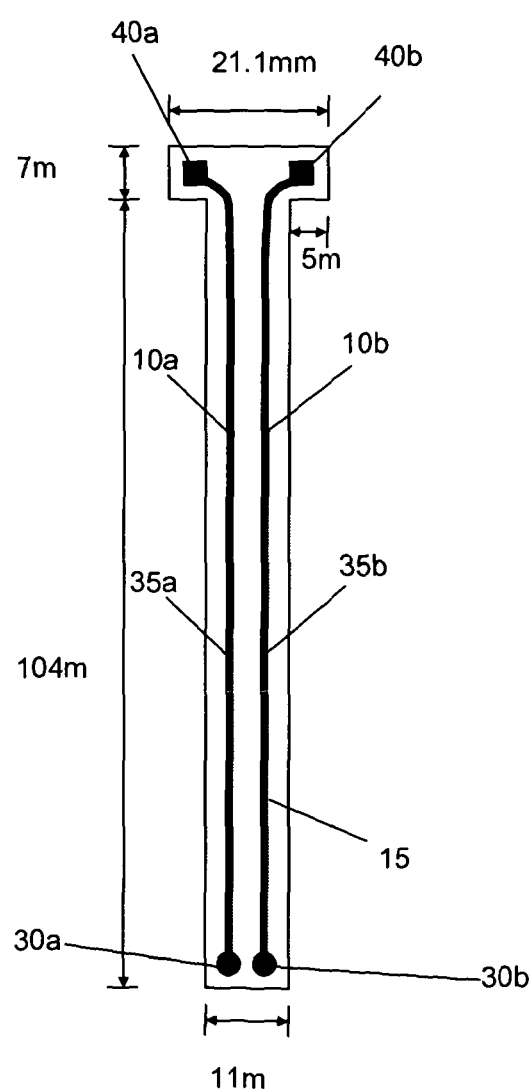
FIG. 5 is a schematic of a partially assembled sensor of FIG. 1 after trimming of excess material.

The surface area of the electrodes 10a, 10b is minimised and the electrodes take the form of an elongate electrode arrangement. The substrate 15 and insulating layers 20 are trimmed close to the electrodes 10a, 10b, as shown in FIG. 5, so that the sensor 5 is long and thin. In this way, obstruction of fluid flow from the wound is minimised. In one embodiment, the electrodes 10a, 10b take the form of microelectrodes. However, for other applications, sensor 5 dimensions between 0.1 mm and 10 cm are sufficient.

Overlying the electrode arrangement, and in particular the sensing surfaces 30a, 30b is the non-adherent porous layer 25. This layer 25 may be made of any suitable material, such as non-adherent silicone coated cellulosic. The non-adherent porous layer 25 is attached to the insulating layer 20 using spotted adhesive attachment via a medical grade ethyl cyanoacrylate adhesive. By covering the sensing surfaces 30a, 30b with the layer 25, this avoids direct physical contact with the wound, but at the same time allows wound fluid or dressing fluid to reach the contacts 30a, 30b, as it flows or leaks into the porous layer 25 from the wound.

By having a porous layer 25 proximate contacts 30a, 30b, there is provide a localised, fixed volume environment in the vicinity of the sensing area. This helps to ensure that a layer of wound fluid in contact with the sensing surfaces 30a, 30b of the electrodes 10a, 10b is of constant thickness in a wet, moist or drying wound. This improves the consistency of electrical measurements of the wound fluid whilst still allowing for exchange of wound fluids to provide reliable readings of the wound status.

The porous layer 25 allows for diffusion of ions and metabolites so that gradual changes in the constituents of the wound fluid, or gradual loss and drying of the wound may give consistent results, even with different dressing types. In effect, the porous layer 25 provides a consistent volume boundary for carrying out measurements. As the preferred current path in the presence of liquid is always through the bounded volume, the sensing surface is effectively contained within a measurement cell, defined by the porous layer, thereby improving measurement consistency. This volumetrically constant measurement arrangement is advantageous for wound characterisation through electrical impedance studies, and AC impedance characterisation in particular.

Figure 7:
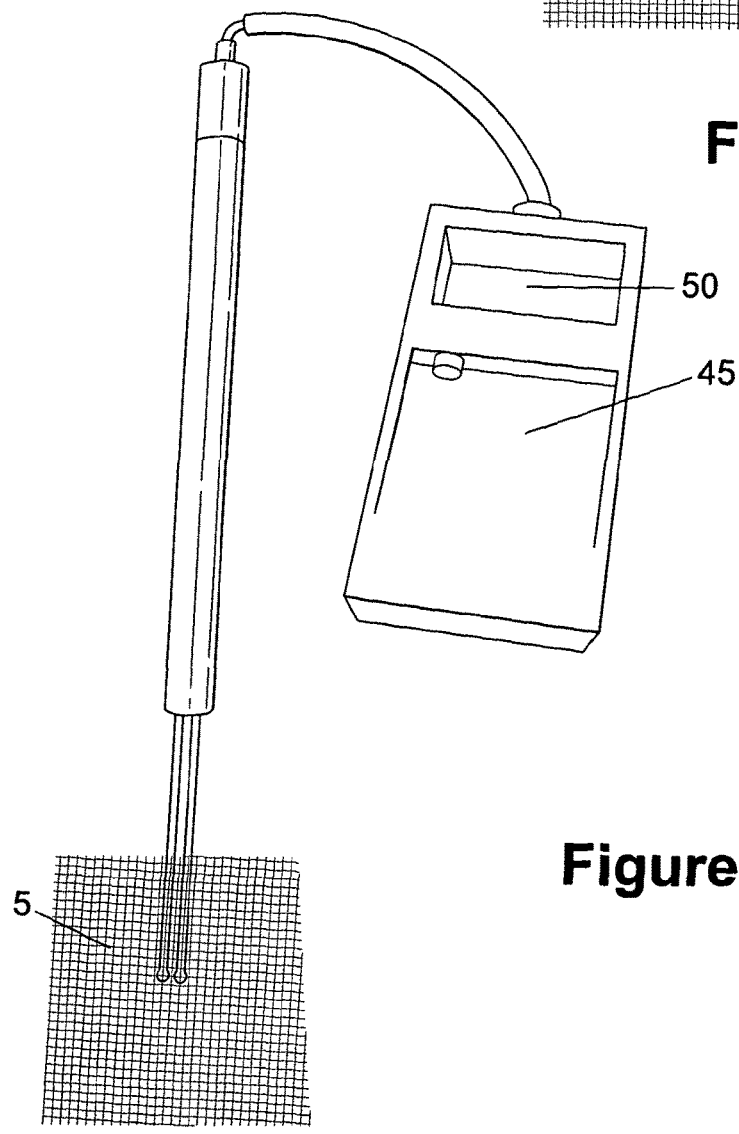
FIG. 7 shows a sensor of FIG. 1 attached to a controller.

In use, the sensor 5 is placed on the wound with the porous layer 25 facing towards the wound and the substrate 15 facing away from the wound. A controller 45 is connected to the contact pads 40a, 40b of the electrodes 10a, 10b, as shown in FIG. 7. The controller 45 is arranged to perform AC impedance measurements using the electrodes 10a, 10b of the sensor 5. The controller 45 is further adapted to calculate the real and imaginary components of the impedance as measured using the electrodes 10a, 10b of the sensor 5. The controller 45 is provided with a processor and memory (not shown). The memory is arranged to store a look-up table. The look-up table maps real and imaginary values of impedance, as measured by the controller 45 via the sensor 5 to corresponding wound states.

The controller 45 is arranged to apply an electrical signal to the electrodes in order to perform electrical stimulation of the wound. The controller 45 may be arranged to apply a current in the order of μA to mA. The controller may be arranged to apply a voltage in the range 5 to 200 mV and a frequency in the range 0.1-100 kHz. Typically the wound sensor/dressing remains in place for one to seven days. Measurements may be taken daily, every two hours or continuously depending on the information needed.

When completely dry, the impedance as measured between the electrodes 10a, 10b tends to an open circuit value and the modulus of the AC impedance is generally sufficient to show this. When completely wet, the controller 45 measures a short circuit between the electrodes 10a, 10b. Varying impedance values between short circuit and open circuit are indicative of varying degrees of moisture in the electrical path between the two electrodes 10a, 10b. Consequently by measuring ac the impedance as a function of time, a temporal measure of the wound dressing hydration can be obtained. This in turn provides an indication of wound healing progress.

The processor of the controller 45 is arranged to determine real and imaginary components of the measured values impedance value and compare them with values stored in the look up table. The processor is operable to retrieve a wound state associated with the measured impedance and provide the wound state to a display 50, to allow an operator to rapidly determine the status of the wound. Some wound states and their associated impedances are detailed in Table 1.

TABLE 1

| Wound Status | Impedance |
| --- | --- |
| Dry | Tending to open circuit |
| Dry with some moisture | Finite but high |
| Moist | Measurable |
| Moist tending to wet | Low |
| wet | Tending to short circuit |

The impedance can be used to determine the properties of the exudates, for example, the viscosity of the exudate. This in turn can be used to determine a healing status of the wound, for example, a change from normal healing to an infection.

The impedance can be tracked with time to provide rates of moisture loss from the wound during healing or specific moisture level behaviour with time and compared to expected data for a specific wound type, thus allowing novel clinical interventions based on measurements such as rates of moisture change, and/or target moisture on a specified day, etc.

By having a protective porous layer 25 that retains wound fluid, the sensor 5 of the present invention may be effective even in a pressurised environment, for example, under a tightly wound bandage or in a compression bandage. This is because the reading obtained from the sensor 5 may be less prone to change as the sensor 5 is pressed into wound tissue, since the wound fluid and moisture in the sensing path is more likely to be retained by the porous layer 25 and less likely to be squeezed out or reduced. In addition, the sensor 5 of the present invention may advantageously be used in negative pressure therapy, as it is relatively resistant to loss of moisture and associated spurious changes in readings.

The sensor 5 may be constructed using any suitable technique. For example, the sensor may be made using two 16 cm by 25 cm sheets of medical grade, non-adhering, low density polyethylene film, coated on one surface with an acrylic adhesive, such as Bioflex (RTM) RX607P, produced by Scapa. The two films are adhered together using facing adhesive surfaces, taking care to exclude air pockets between the sheets, to form the substrate. As an example, the substrate 15 may be approximately 0.15 mm thick.

The substrate is then placed in a screen-printing frame. A screen of the screen-printing frame is patterned to produce the shape of the electrodes 10a, 10b, including the sensing surfaces 30a, 30b, the signal carrying portions 35a, 35b and the contact pads 40a, 40b. A silver/silver chloride ink, is then screen printed into electrode patterns on the substrate 15. The substrate 15, printed with the silver/silver chloride ink patterns in the shape of the electrodes 10a, 10b, is then heated at 80° C. for 30 minutes in order to cure the ink and form the electrodes 10a, 10b.

A further layer of medical grade low density polyethylene film is then adhered onto the signal carrying portion 35a, 35b of the electrodes 10a, 10b and surrounding parts of the substrate 15 using a medical grade acrylic adhesive coated onto one surface of the polyethylene film in order to form the insulating layer 20. As an example, the insulating layer 20 is approximately 0.076 mm thick.

Figure 3:
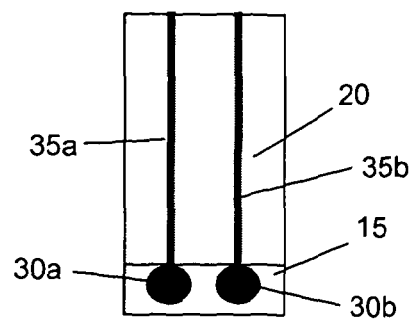
FIG. 3 is a schematic of application of an insulating overlay as part of a method of production of the sensor of FIG. 1.
Figure 4:
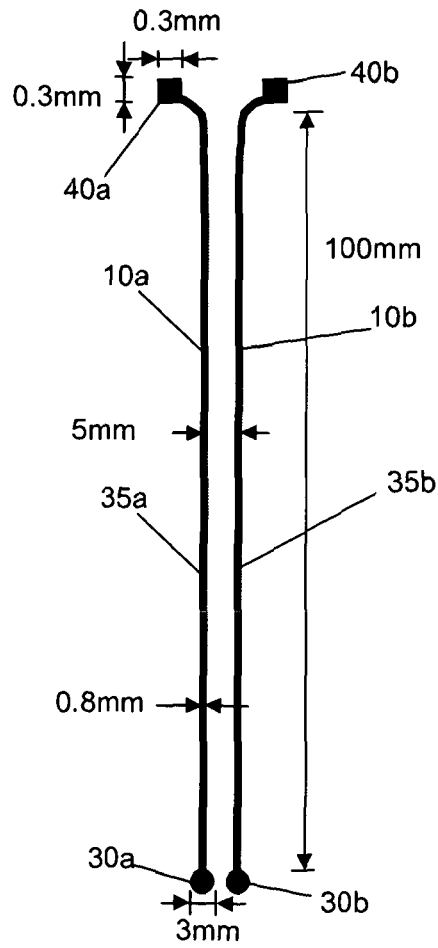
FIG. 4 is a schematic of an electrode arrangement of the sensor of FIG. 1.

The insulating layer 20 extends to the edge of the sensing surface 30a, 30b of the electrode 10a, 10b, as shown in FIG. 3, such that the sensing surface 30a, 30b is left exposed, whilst the signal carrying portion 35a, 35b of the electrode 10a, 10b is sealed between the substrate 15 and the insulating layer 20. A cutter is used to remove excess substrate 15 and insulating layer 20 such that the surface area is minimised, as shown in FIG. 5. Insulated copper wire for connecting to the controller 45 is attached to contact pads 45a, 45b of the electrodes 10a, 10b using a conductive epoxy.

Figure 6:
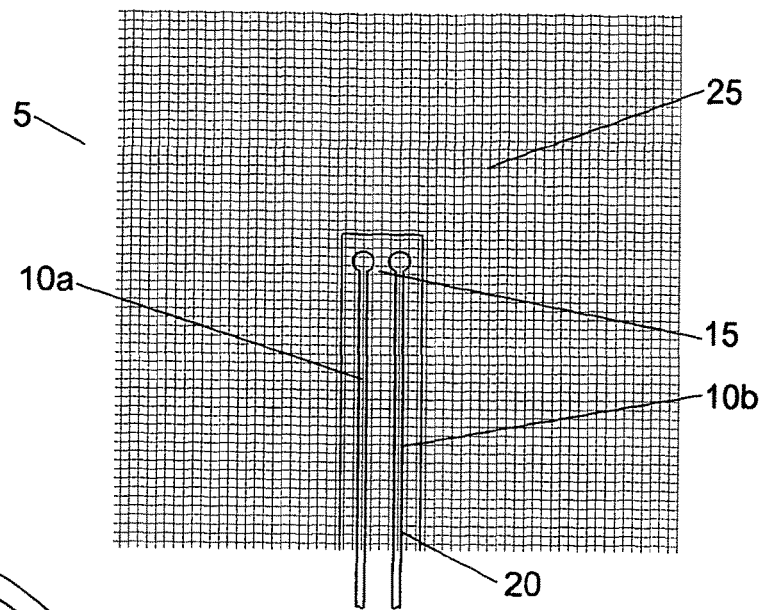
FIG. 6 is a schematic showing the attachment of a non-adherent porous layer as part of the fabrication of the sensor of FIG. 1.

A silicone coated rolled viscose porous layer 25 is then attached, as shown in FIG. 6, with the sensing surfaces 30a, 30b of the electrodes 10a, 10b facing towards, and adjacent, the porous layer 25. To do this, the porous layer 25 is coated with primer and the outer surface of the insulating layer 20 and/or the exposed substrate 15 is spotted with medical grade ethyl cyanoacrylate adhesive. Then the porous layer 25 is attached to the adhesive spotted surfaces to form the sensor 5. After attachment of the porous layer 25, the sensor 5 can be sterilised using ethylene oxide.

Figure 8:
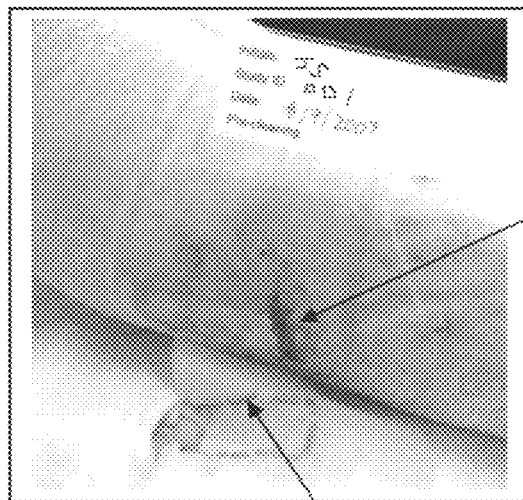
FIG. 8 shows a wound dressed with the wound dressing of the invention at two healing stages.
Figure 8:
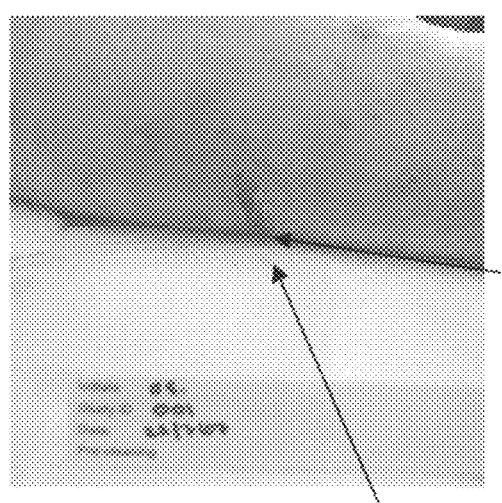

The device of the present invention allows optimal wound healing and monitoring. FIG. 8 shows the effects of using the non-adherent sensor as described herein when applied to a patient with a leg ulcer wound. Week 3 of healing the wound is still wet to moist (3.142 kΩ). Week 4 the ulcer has healed and the wound is dry (305 kΩ)). Because of the non-adherent porous layer, there is no adhesion of the sensor device to the skin and the ulcer has healed well.

A skilled person will appreciate that variations of the disclosed arrangements are possible without departing from the scope of the invention. For example, although embodiments of the above invention have been described as electrodes 10a, 10b that have been formed by screen-printing onto the substrate 15 using a suitable ink, in practice, other electrode arrangements could be used. For example, the electrodes 10a, 10b could be formed of wire. Although the electrodes 10a, 10b are described as advantageously being formed from silver/silver chloride, other electrode compositions could be used, such as copper, gold, platinum or carbon based electrodes.

In addition, although the porous layer 25 is described as comprising a silicone coated rolled viscose sheet, other non-adherent porous materials may be used. Furthermore, although in the embodiments above, the substrate 15 and insulating layer 20 are constructed from low-density polyethylene tape, other non-adherent biocompatible materials could be used. Although the sensor 5 described above is advantageously used to monitor AC impedance, the sensor 5 may additionally or alternatively be used in a range of electrical based measurements and/or procedures, such as pH measurement, conductivity measurement and/or electrical stimulation of the wound. Also, the sensor 5 may be provided separately, or integrated with or bonded to a wound dressing. Accordingly the above description of the specific embodiment is made by way of example only and not for the purposes of limitation. It will be clear to the skilled person that minor modifications may be made without significant changes to the operation described.

The invention claimed is:

1. A wound sensor comprising:
at least one electrode and an external measurement device coupled or configured to couple with the at least one electrode, the external measurement device being configured to receive electrical measurement signals from the at least one electrode and to determine impedance of a wound or wound fluid using the received electrical measurement signals, the at least one electrode having a sensing surface and a signal carrying portion, the signal carrying portion being configured for carrying the electrical measurement signals from the sensing surface to the external measurement device, the signal carrying portion and the sensing surface both being disposed on an electrically insulating substrate having insulating properties during use of the wound sensor;
an insulating layer that covers said signal carrying portion, such that said signal carrying portion is positioned between the substrate and the insulating layer; and a non-adherent porous layer in direct contact with the sensing surface, wherein:
said sensing surface is positioned between the substrate and the non-adherent porous layer that is in direct contact with the sensing surface, such that the non-adherent porous layer that is in direct contact with the sensing surface and the substrate at least partly define a bounded volume in which the sensing surface is provided; and
the non-adherent porous layer directly overlies and contacts the sensing surface, forms a wound contact surface, and collects a volume of wound fluid within the bounded volume that is measurable by the external measurement device using the at least one electrode to determine the impedance.

2. A wound sensor according to claim 1, wherein the non-adherent porous layer is a biocompatible and/or non-irritant surface, material or coating.

3. A wound sensor according to claim 1, wherein the sensor comprises two or more electrodes.

4. A wound sensor according to claim 1, wherein the at least one electrode is printed.

5. A wound sensor according to claim 1, wherein the non-adherent porous layer is separate from the at least one electrode.

6. A wound sensor according to claim 1, wherein the non-adherent porous layer fully covers the at least one electrode.

7. A wound sensor according to claim 1, wherein the non-adherent porous layer is non-conducting.

8. A wound sensor according to claim 1, wherein the non-adherent porous layer is adjacent to at least part of the at least one electrode.

9. A wound sensor according to claim 1, wherein the sensor is arranged such that the non-adherent porous layer is provided on an opposite side of the at least one electrode to the substrate.

10. A wound sensor according to claim 1, wherein the non-adherent porous layer comprises silicone.

11. A wound sensor according to claim 1, wherein the non-adherent porous layer comprises a cellulosic material.

12. A wound sensor according to claim 1, wherein the non-adherent porous layer is between 50 500 pm thick.

13. A wound sensor according to claim 1, wherein the sensing surface is configured for taking electrical measurements.

14. A wound sensor according to claim 1, wherein the at least one electrode comprises a biocompatible material.

15. A wound sensor according to claim 1, wherein the at least one electrode is selected from the group consisting of silver, a silver compound, and silver chloride.

16. A wound sensor according to claim 1, wherein the at least one electrode is at least partially formed from conductive ink.

17. A wound sensor according to claim 1, wherein the at least one electrode is elongated.

18. A wound sensor according to claim 1, wherein at least part of a signal carrying portion of the at least one electrode is provided between the substrate and the insulating layer and the sensing surface is not covered by the insulating layer.

19. A wound sensor according to claim 1, wherein the insulating layer is at least one of adhered to or pressed together with or integral with the substrate around a signal carrying part of the at least one electrode.

20. A wound sensor according to claim 1, wherein the substrate or the insulating layer comprise a biocompatible, flexible polymer film.

21. A wound sensor according to claim 1, wherein at least one of the substrate and the insulating layer comprises a polyolefin film.

22. A wound sensor according to claim 21, wherein the substrate or the insulating layer is at least partially coated with an adhesive.

23. A wound sensor according to claim 1, wherein the substrate is between 0.075 mm and 1 mm thick.

24. A wound sensor according to claim 1, wherein the wound sensor is arranged to be used with a wound dressing.

25. A wound sensor according to claim 24, wherein the wound sensor is arranged such that, in use, the substrate faces the wound dressing, whilst the non-adherent porous layer and the exposed sensing surface of the at least one electrode face the wound.

26. A wound sensor according to claim 1, wherein each of the sensing surface of the at least one electrode are arranged to perform electrical stimulation of the wound.

27. A wound sensor according to claim 1, wherein a pair of electrodes is adapted to measure wound hydration.

28. A wound sensor as claimed claim 1, wherein the at least one electrode comprises a signal measurement part connected to the signal carrying portion for allowing communication of measurements from the signal measurement part.

29. A wound sensor as claimed in claim 28, wherein the signal carrying portion of the at least one electrode is substantially electrically insulated from the wound environment.

30. A wound sensor as claimed in claim 28, wherein the signal carrying portion is covered by an electrically insulating layer.

31. A wound sensor according to claim 10, wherein the non-adherent porous layer comprises a silicone coating.

32. A wound sensor according to claim 12, wherein the non-adherent porous layer has pore sizes in the range of 20-500 pm.

33. A wound sensor according to claim 19, wherein the insulating layer is pressed together with the substrate around the signal carrying part of the electrode.

34. A wound sensor according to claim 19, wherein the insulating layer is integral with the substrate around the signal carrying part of the at least one electrode.

35. A wound sensor according to claim 21, wherein the polyolefin film is a polyethylene film.

36. A wound sensor according to claim 22, wherein the adhesive is an acrylic adhesive.

37. A wound sensor according to claim 1, wherein the at least one electrode is planar.

38. A wound sensor according to claim 1, wherein the electrically insulating substrate is either a biocompatible, flexible polymer film or a polyolefin film.

39. A wound sensor according to claim 1, wherein at least one of:
the signal carrying portion is sandwiched between the insulating layer and the electrically insulating substrate;
the insulating layer is bonded to the electrically insulating substrate around the signal carrying portion; or
the insulating layer and the electrically insulating substrate are both trimmed close to the at least one electrode so that the wound sensor has a long and thin shape.

40. A wound sensor according to claim 1, wherein the external measurement device is configured to deliver electrical signals to the at least one electrode for analyzing the wound environment.

41. A wound sensor according to claim 1, wherein the external measurement device is configured to deliver electrical current or voltage to the wound or wound fluid.

42. A wound dressing comprising: a wound sensor, and an external measurement device, the external measurement device being:
coupled or configured to couple with the wound sensor, and configured to receive electrical measurement signals from the wound sensor and to determine impedance of a wound or wound fluid using the received electrical measurement signals,
the wound sensor comprising:
at least one electrode having a sensing surface and a signal carrying portion, the signal carrying portion being configured for carrying the electrical measurement signals from the sensing surface to the external measurement device, the signal carrying portion and the sensing surface both being disposed on an electrically insulating substrate having insulating properties of during use of the wound sensor;
an insulating layer that covers said signal carrying portion, such that said signal carrying portion is positioned between the substrate and the insulating layer; and
a non-adherent porous layer in direct contact with the sensing surface,
wherein:
said sensing surface is positioned between the substrate and the non-adherent porous layer that is in direct contact with the sensing surface, such that the non-adherent porous layer that is in direct contact with the sensing surface and the substrate at least partly define a bounded volume in which the sensing surface is provided; and
the non-adherent porous layer directly overlies and contacts the said sensing surface, forms a wound contact surface, and collects a volume of wound fluid within the bounded volume that is measurable by the external measurement device using the at least one electrode to determine the impedance.

43. A wound dressing according to claim 42, wherein the at least one electrode is planar.

44. A method of determining a property of a wound, said method comprising the steps of:
providing a wound sensor according to claim 1; and
determining impedance using the wound sensor.

45. A method according to claim 44, comprising determining impedance using AC impedance spectroscopy.

46. A method according to claim 45, comprising using the determined impedance to determine a wound status such as a level of moisture present and/or viscosity of exudate from a wound and/or whether a wound is becoming infected.

47. A method according to claim 44, comprising leaving the wound sensor in communication with the wound during healing.

48. A method according to claim 44, comprising determining time duration or time related healing of the wound.

49. A method according to claim 48, comprising determining changes in moisture.

50. A method according to claim 44, comprising placing the wound sensor on a wound such that the non-adherent porous layer faces the wound, such that the non-adherent porous layer is located between the electrodes and the wound.

51. A method of fabrication of a sensor, said method comprising the steps of: providing a wound sensor according to claim 1; and
positioning the non-adherent porous layer adjacent the sensing surface of the at least one electrode.

52. A method according to claim 51, further comprising the step of providing a patterned ink layer on at least part of the substrate and processing the patterned ink to form the at least one electrode.

53. A method according to claim 52, wherein the ink comprises at least one metallic substance and a metal salt selected from the group consisting of silver, gold, platinum, carbon, graphite, and a compound thereof.

54. A method according to claim 53, wherein the ink is selected from the group consisting of a silver, a silver salt, and a silver chloride.

55. A method according to claim 52, wherein the ink pattern is applied by screen printing.

56. A method according to claim 51, further comprising the steps of:
applying an insulating layer to at least part of the at least one electrode and substrate, and
leaving a portion of the at least one electrode uncovered by the insulating layer.

57. A method according to claim 55, further comprising the step of removing an excess of at least one of the substrate and insulating layer.

58. A method according to claim 51, wherein the non-adherent porous layer is adhesively attached using a medical device adhesive.

59. A method according to claim 58, wherein the medical device adhesive is an acrylate adhesive such as a cyanoacrylate adhesive.

* * * * *

UNITED STATES PATENT AND TRADEMARK OFFICE
CERTIFICATE OF CORRECTION

Page 1 of 1

PATENT NO. : 10,716,490 B2
APPLICATION NO. : 13/379309
DATED : July 21, 2020
INVENTOR(S) : Patricia Connolly It is certified that error appears in the above-identified patent and that said Letters Patent is hereby corrected as shown below:

In the Claims

Claim 21, Column 12, Line 37:
"one of the substrate and the insulating layer comprises a"
Should read:
-- one of the substrate or the insulating layer comprises a --

Claim 42, Column 14, Line 5:
"the said sensing surface, forms a wound contact"
Should read:
-- the sensing surface, forms a wound contact --

Signed and Sealed this
Second Day of March, 2021

Drew Hirshfeld
*Performing the Functions and Duties of the
Under Secretary of Commerce for Intellectual Property and
Director of the United States Patent and Trademark Office*